United States Patent [19]

Acharya et al.

[11] Patent Number: 5,103,823
[45] Date of Patent: Apr. 14, 1992

[54] MOTION CORRECTION IN CARDIOLOGY INSPECTION SYSTEMS

[75] Inventors: Kishore C. Acharya, Brookfield; Raymond P. Grenier, Milwaukee, both of Wis.

[73] Assignee: Scinticor Incorporated, Milwaukee, Wis.

[21] Appl. No.: 409,249

[22] Filed: Sep. 19, 1989

[51] Int. Cl.⁵ .............................................. A61B 6/00
[52] U.S. Cl. ................................. 128/653.1; 128/654; 250/363.04
[58] Field of Search ................ 128/653 R, 654, 659; 250/363.02, 363.04, 363.03, 363.07, 363.09, 369, 390.03, 363.08; 364/413.22, 413.23, 413.24

[56] References Cited

U.S. PATENT DOCUMENTS

| | | | |
|---|---|---|---|
| 3,670,715 | 6/1972 | Perilhou et al. | 128/659 |
| 3,769,967 | 11/1973 | Jones et al. | 128/653 R |
| 4,033,335 | 7/1977 | Nickles | 128/659 |
| 4,058,728 | 11/1977 | Nickles | 250/369 |
| 4,197,836 | 4/1980 | Wagner et al. | 128/659 |
| 4,258,428 | 3/1981 | Woronowicz | 250/369 |
| 4,281,382 | 7/1981 | Knoll et al. | 364/413.24 |
| 4,458,688 | 7/1984 | Von Behren | 128/659 |
| 4,466,075 | 8/1984 | Groch et al. | 250/363.07 |
| 4,475,042 | 10/1984 | Arseneau | 250/369 |
| 4,483,342 | 10/1984 | Pfeifer | 128/653 R |
| 4,544,949 | 10/1985 | Kurihara | 128/654 |
| 4,559,597 | 12/1985 | Mullani | 250/363.03 |
| 4,573,122 | 2/1986 | Inbar et al. | 250/363.07 |
| 4,632,123 | 12/1986 | Govaert et al. | 128/654 |
| 4,839,808 | 6/1989 | Koral et al. | 364/413.24 |
| 4,846,187 | 7/1989 | Siegel | 128/659 |

Primary Examiner—William E. Kamm
Assistant Examiner—Scott R. Akers
Attorney, Agent, or Firm—Reinhart, Boerner, Van Deuren, Norris & Rieselbach

[57] ABSTRACT

A method and apparatus for motion correction of image information collected by a cardiology inspection system. The cardiology inspection system collects image information from an exercising patient. The system corrects for the patient motion to provide dynamic time segmented images of radioactive dye flow through the patient's cardiac system, removing anomalous displacements from the images and allowing unambiguous evaluation of heart functionality while under physical stress.

11 Claims, 5 Drawing Sheets

Microfiche Appendix Included
(1 Microfiche, 73 Pages)

MOTION CORRECTION IN CARDIOLOGY INSPECTION SYSTEMS

A microfiche appendix of one page comprising 73 frames is part of this application, said appendix including computer programs and data output therefrom.

BACKGROUND OF THE INVENTION

The present invention relates generally to a method and apparatus for motion correction of image information collected in a cardiology inspection system, such as, a radionuclide angiographic system. More particularly, the invention is related to a method and apparatus for generating a dynamic set of time segmented images showing fluid flow properties within a patient's cardiac system having a radioactive dye passing through.

In the general field of diagnostic cardiology an array of new methodologies have been developed to evaluate the human cardiac system for purposes of diagnosing cardiac disease conditions and providing clinically useful information to the diagnostician. For example, it is known that useful information can be obtained by evaluating the fluid flow properties of the left ventricle of the heart. While such evaluations have lead to substantial improvement in the diagnosis and treatment of cardiac disease, substantial impediments still prevent reliable evaluation of cardiac disease conditions which might be revealed by substantially real time imaging of the cardiac system of a patient under physical stress, such as while exercising on a treadmill or exercise bicycle. Nuclear radiographic techniques are severely restricted by artifacts which can be introduced into the images by the motion of an exercising patient. Thus, evaluation of the details of such motion affected, nuclear radiographic data is more difficult and the results are frequently quantitively comprimised.

BRIEF SUMMARY OF THE INVENTION

It is a primary objective of the invention to provide an improved apparatus and method for correcting the effect of patient motion on diagnostic images of fluid flow in the human cardiac system.

It is another object of the invention to provide a novel apparatus and method for removing the effect of patient exercise motion from dynamic images of radioactive dye flow in the patient's cardiac system.

It is a further object of the invention to provide an improved apparatus and method for removing the effects of anomalous displacement from images of the human heart during patient exercise, allowing unambiguous evaluation of heart functionality while under physical stress.

It is an additional object of the invention to provide a novel apparatus and method for using the centroid of fluid flow in a selected region of the human cardiac system to substantially eliminate extraneous patient motion induced artifacts from dynamic images of fluid flow through the patient's cardiac system.

DETAILED DESCRIPTION

Figure 1:
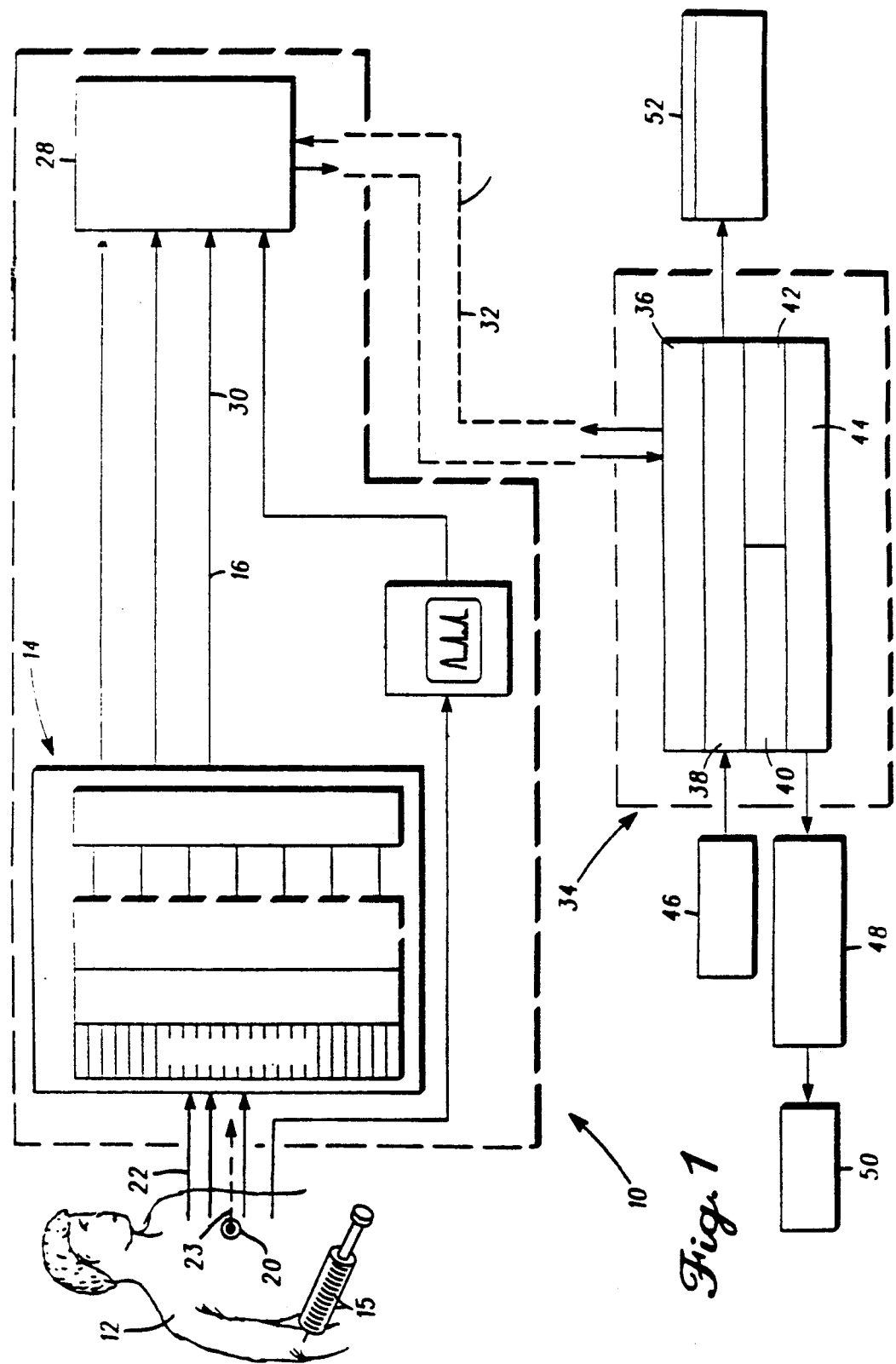
FIG. 1 is a functional block diagram of a radionuclide angiographic system.

Referring to FIG. 1, a conventional radionuclide angiographic system (such as, for example, a Baird Atomic System 77) is shown generally at 10. Aspects of such a system are described in U.S. Pat. No. 4,267,452 which is incorporated by reference herein. In FIG. 1 patient 12 is exercising, (such as on a treadmill—not shown) and a radiation detector 14, such as, a conventional multicrystal scintillator camera (also see U.S. Pat. No. 4,267,452), is positioned at a selected location to sense radiation. The radiation detector 14 can be positioned in various orientations in order to collect image data frames characteristic of different perspectives of the patient's cardiac system. In the illustrated embodiment the radiation detector 14 is positioned to evaluate the vertical elevation image of the left ventricle of the patient 12. The radiation typically used is gamma radiation emitted from a radioactive dye, (not shown) such as, for example, a $^{99m}$Tc pertechnetate solution (which is often followed by a saline "chaser"). The radioactive dye is injected into the patient 12 in the conventional manner of first pass radionuclide angiography (such as by a syringe 15 containing the radioactive dye). (see, for example, U.S. Pat. No. 4,033,335 which is incorporated by reference herein.) The radiation emitted from the radioactive dye is sensed by the radiation detector 14 which generates a two dimensional matrix of electronic signals 16 (an image data frame) characteristic of the intensity of radiation emitted from a particular volume projected spatial area of the patient's body. A pluality of such image data frames are collected over time as the radioactive dye passes through the patient's cardiac system. The angiographic system 10 therefore rapidly accumulates over a relatively short time period the electronic signals 16 in the form of a plurality of time segmented image data frames. For each image data frame an integration of detected signal is carried out over a period of roughly fifty milliseconds. The electronic signals 16 are collected from the patient over a total time of about a minute. These plurality of image data frames are stored in an electronic memory for further manipulation, and several different methodologies can be applied for correcting for the extraneous patient motion.

Figure 2A:
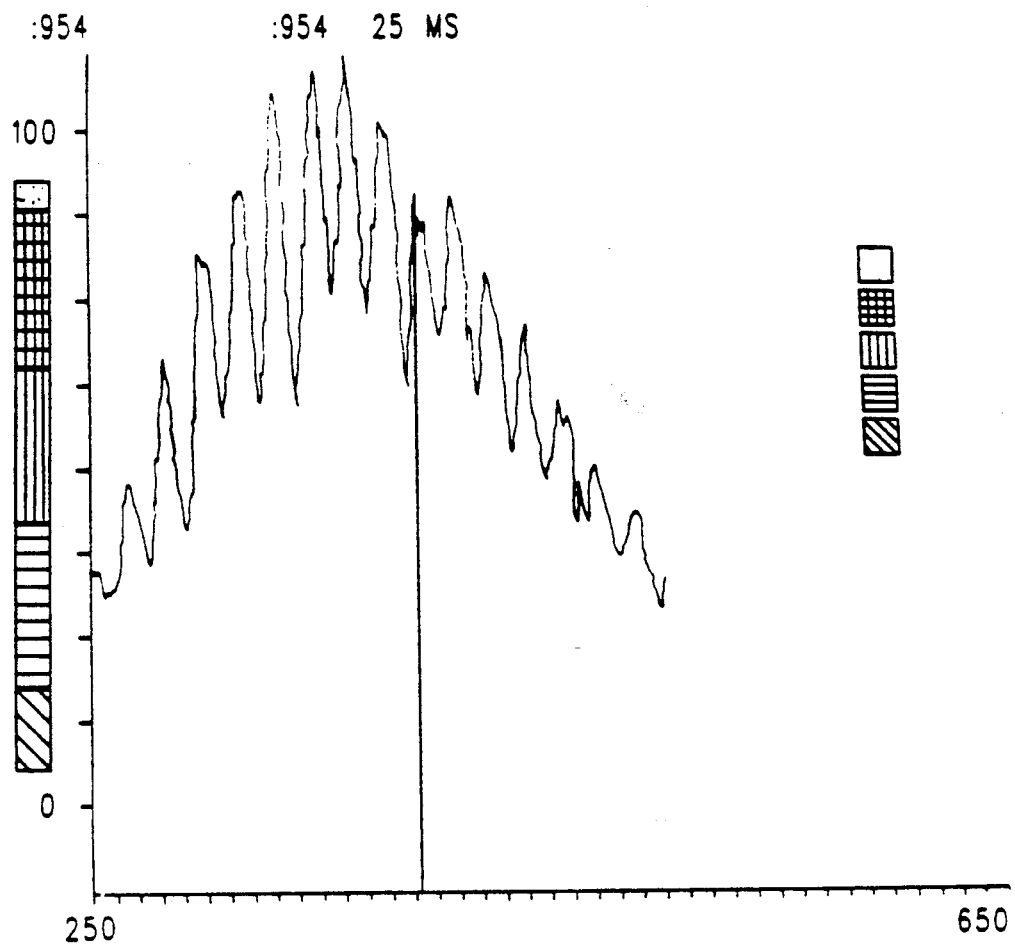
FIG. 2A illustrates a histogram before motion correction of electronic signal amplitudes for a plurality of cardiac cycles in a designated livo phase.
Figure 2B:
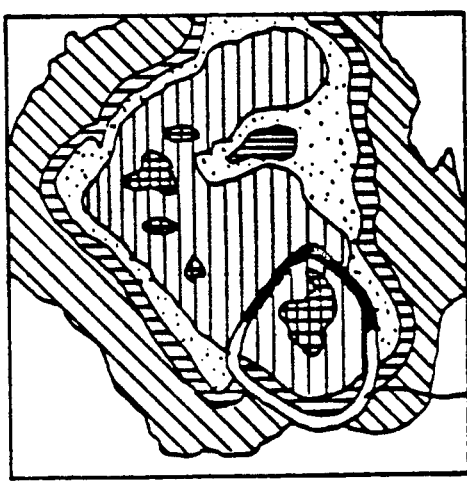
FIG. 2B shows an image data frame before motion correction of electronic signals at end diastole of a cardiac cycle with a region of interest marker boundary.

FIG. 2A illustrates a histogram of the integrated intensity of the electronic signals within a region of interest 18 shown in FIG. 2B (outlined area at lower right of image data frame). The histogram of FIG. 2A is characteristic of the behavior of the integrated intensity before correction for extraneous patient motion. The histogram peak of each cardiac cycle is associated with fluid flow at end diastole, and the minimum is associated with end systole. Note that the trace of the peak values is substantially a smooth curve, while the trace of the minimum values is relatively irregular. After selected motion correction, in a manner to be described in more detail hereinafter, both the trace of the peak and the minimum values form a substantially smooth curve (compare FIG. 3A after correction). This aspect of improvement of the trace of the minimum in the histogram is one figure of merit in evaluating the reliability of the motion correction. Other time segments within each cardiac cycle can also be characterized by the method of the invention, and a histogram can be constructed and analyzed for other selected regions of interest of the cardiac system.

Correction for extraneous human motion in evaluating cardiac flow performance can involve, for example, removal of motion artifacts arising from exercise used to generate physical stress on the patient's cardiac system. In using the first pass radionuclide angiographic system 10 of FIG. 1, motion correction can generally be divided into two categories, major magnitude (vigorous treadmill exercise, e.g.) and minor magnitude motion (prone bicycling exercise, e.g.) corrections. Correction for major motion can be accomplished by two methodologies, a dual energy method and a single energy method.

In the dual energy method of motion correction, primary and secondary isotope sources are used to gather radiation data simultaneously in order to implement motion correction. The principal photopeaks of the two isotopes should be separated in energy as much as possible in order to optimize energy resolution to enhance isolation of the desired photopeak signal. This is desirable in order to establish the relative centroids of radiation emitted from both the primary isotope (such as a radioactive dye injected into the patient) and from the radiation emitted by a secondary isotope which acts as a reference point. In a preferred embodiment, the primary isotope source is $^{99m}$Tc which has the principal photopeak at 140 keV. The secondary isotope source is a point source of $^{241}$Am (or other such conventional radio-pharmaceutical) with the principal photopeak at 60 keV. Other secondary radioactive sources include a radioactive iodine and thallium. It is generally preferred to have the principal and secondary isotope photopeaks separated by at least 50 keV to achieve the desired good resolution as described above. The reference source, a secondary isotope point point source 20 is attached to the patient 12 as shown in FIG. 1. The patient 12 undergoes exercise, such as walking on a treadmill (not shown), to achieve a prescribed level of physical stress on the patient's cardiac system. Once the prescribed stress level is reached the radioactive fluid, or dye, is injected into the patient 12. As the injected radioactive fluid passes thru the patient's cardiac system, radiation 22 is emitted from the patient 12 and is sensed by a detector, such as, for example, the radiation detector 14, or the multicrystal NaI(Th) camera (hereinafter, the camera 14) shown in FIG. 1. Simultaneously, the camera 14 senses the radiation 23 emitted by the secondary isotope point source 20. As described hereinbefore, when the radioactive fluid circulates through the patient's cardiac system, a plurality of the time segmented image data frames are generated. The radiation 22 emitted by the radioactive fluid is sensed by the camera 4 and is converted in a conventional manner into the electronic signals 16. These electronic signals 16 are stored in an electronic memory, such as random access memory, contained in frame processor CPU 28. At the same time, the radiation 23 emitted by the secondary isotope point source 20 is detected by the camera 24 and is converted in a conventional manner into a reference signal 30 which can be stored in an electronic memory, such as a random access memory in the frame processor CPU 28. Each of the time segmented image data frames include a two dimensional array of data characteristic of the intensity of radiation from a volume projected area of the patient's cardiac system under study. These electronic signals 16 are eventually converted into a video display for review by the operator or diagnostician (collection and display of such data is well known, as set forth in U.S. Pat. No. 4,245,244 which is incorporated by reference herein).

The raw data of the image data frames is output through a fiber optic link 32 to a computer system 34, such as, for example, an Apple MAC II including a conventional fiber optic link interface 36, a central processing unit 38, a floppy disk unit 40, a built in hard disk 42 and a conventional video processing card 44. Input/output functions are provided in a conventional manner by keyboard 46, hard copier/printer 48 and video monitor 50. Also shown in FIG. 1 is an optional electronic mass storage unit 52 coupled to the computer system 34.

The computer system 34 operates on the raw image data frame information to provide corrections for extraneous noise and background and also to remove the effects of patient motion. The extraneous noise and background can be removed both from the reference signal 30 and the electronic signal 16. The reference signal 30 associated with the secondary isotope source 20 is treated for background noise by determining the centroid of each time segmented image data frame. The mathematical manipulation necessary for this calculation is performed using computer software included as a microfiche appendix this Specification. Illustrative data associated with patient motion and its corrected form are also included as part of the microfiche appendix. Various methods can be chosen to zero the background, including, e.g., using the computer system 34 in conjunction with the computer software to display on the video monitor 50 the raw values of the reference signal 30. A rectangular box of selected width and height can be placed on the centroid of the reference signal 30 associated with the displayed position of the secondary isotope source 20. All values of the reference signal 30 in the image data frames outside the box are set to zero. The width and height of the box are typically established to insure inclusion of all the reference signals 30 associated with the secondary isotope source 30. A second method of zeroing the background involves determining the maximum and minimum excursion dimensions of the centroid of the reference signal 30 from the secondary isotope source 20 over all the image data frames. All values of the reference signal 30 are set to zero outside the rectangular box dimensions which are set by the maximum absolute value excursion dimension in $+x$, $-x$, $+y$ and $-y$ direction for the centroid.

In a preferred form of the invention, a preprocessing step is applied to the raw data by performing a scatter correction which removes the well known Compton scattering component when the radiation is gamma or energetic X-rays. In addition, a noise filtration step is carried out. The Compton scattering is corrected for by setting a threshold level which is a constant fraction of the electronic signal 16 associated with the radiation 22 emitted from the radioactive fluid. This threshold level is subtracted from the reference signal 30; and it is typically a matter of user discretion to select a threshold level which adequately removes the Compton scattering effect, but does not remove true signal. The noise filtration step is associated with removal of electronic noise and natural background radiation noise. In this step the peak data value of the electronic signal 20 is determined for each of the reference image data frames corrected for the Compton scattering. Any portion of the electronic signal 16 which is below a specific fraction of the peak value is set to zero, while data values above the threshold level are left unchanged. This step is performed using conventional computer software.

The next step in processing the image data frames is to determine the area centroid of the background and noise corrected reference signal 30 for each of the image data frames. The average centroid for the reference signal 30 is then calculated for all the reference image data frames taken. Each of the image data frames containing the electronic signals 16, arising from the radioactive fluid, is repositioned. The desired final video signals, corrected for patient motion, are achieved by moving the electronic signals 16 the incremental spatial difference between the centroid of the particular image data frame of the reference signal 30 and the associated corresponding average centroid of the reference signal 30.

Figure 3B:
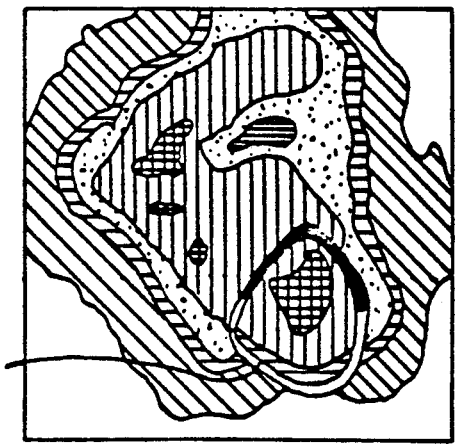
FIG. 3B shows an image data frame after motion correction of electronic signals at end diastole of a cardiac cycle with a region of interest marker boundary.
Figure 4A:
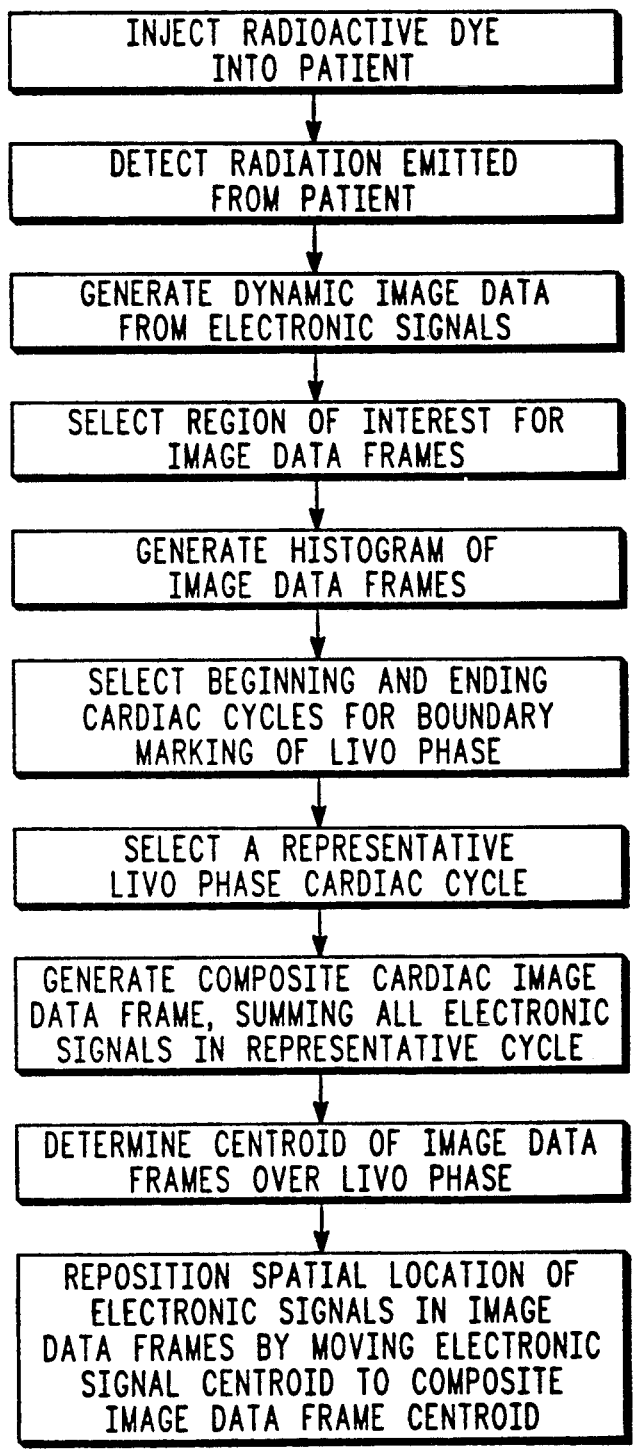
FIG. 4A is a functional block diagram illustrating the steps in implementing computer software for manipulating data to provide corrections for large patient motion, using a single energy radioactive source
Figure 4B:
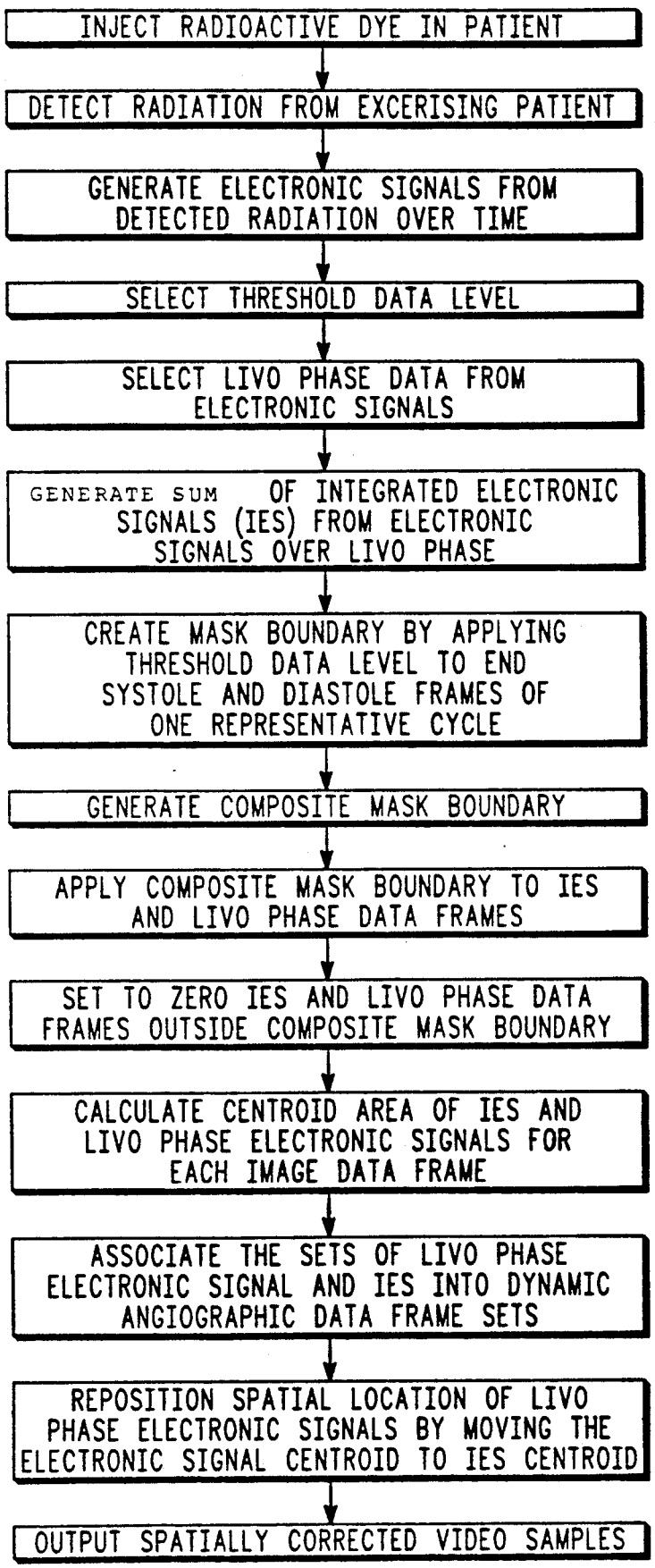
FIG. 4B is a functional block diagram showing the steps of computer software for manipulating data to provide corrections for small patient motion using a single energy radioactive source.

As mentioned hereinbefore, correction for larger, or major magnitude patient motion can also be accomplished by a single energy method. In this methodology only the primary isotope radiation source is used, and there is no secondary reference source. The electronic signal 16 associated with radiation emitted by the radioactive fluid is sensed by the camera 14 in the same manner as for the dual energy method described hereinbefore. In this single energy method the motion uncorrected form of the electronic signals 16 is displayed as image data frames on the video monitor 50. Using the computer system 34 in association with conventional computer software by which motion correction can be accomplished in a manner generally set forth in the flowsheet of FIG. 4A. In this methodology, the region of interest 18 can be drawn by the user, typically encompassing the electronic signals 16 for the ventricle region of the patient 12 (see FIGS. 2B and 3B). A histogram of the type shown in FIG. 2 is generated for the time period of passage of the radioactive fluid through the cardiac system of the patient 12. The histogram includes a plurality of peaks representative of a plurality of complete cardiac cycles. The user then selects a representative portion of these cardiac cycles by denoting a beginning and ending cardiac cycle. This denoted portion of the plurality of cardiac cycles of the histogram is the "livo phase". This livo phase is believed to contain the most representative data for analysis of the patient's cardiac system during a prescribed level of physical stress. The user further selects one representative cardiac cycle within the livo phase, and a composite (or representative) cardiac image data frame is generated by summing all of the electronic signals 16 accumulated during this representative cardiac cycle. A threshold background signal is then selected by the user, and the threshold background is removed from the representative image data frame and also from the image data frames of the plurality of cardiac cycles in the livo phase. Additional extraneous noise signals can be removed in the manner described hereinbefore for the dual energy processing method for motion removal. Once the background and noise corrections are made, the centroids are then determined for the representative image data frame and for each of the image data frames of the plurality of cardiac cycles in the livo phase. The spatial location of the electronic signals 16 making up the image data frames is repositioned by moving the centroid in each image data frame to the centroid location for the composite image data frame. These repositioned data values are the desired video signals which have been corrected for motion.

Another aspect of the invention is the ability to remove extraneous patient motion associated with relatively small displacement motion compared to the previously described "large" or major magnitude motion. This procedure can be implemented for situations, such as, for example, when the patient 12 is using an exercise bicycle, or performing other moderate exercise motion. This procedure can also be used as a second stage refinement of patient data already corrected for major patient motion by one of the techniques described hereinbefore. In this methodology of removing small or minor magnitude motion, the electronic signals 16 are generated and collected in the same manner described previously. The background noise correction can likewise be applied in the manner described hereinbefore. In this correction, the user typically selects a threshold fractional cutoff level by viewing the end diastole image of the selected representative cardiac cycle and establishing the signal level at which the noise vanishes outside the projected image of the cardiac system being inspected.

In a preferred embodiment, all the image data frames of the electronic signals 16 are interpolated in a conventional manner to increase the pixel data from a $20 \times 20$ array to an $80 \times 80$ array which is stored in the memory unit of the frame processor CPU 28. The threshold level is applied to the interpolated end diastole and end systole image data frames of the representative cardiac cycle. Each of the representative cycle image data frames comprise an integrated electronic signal which is created by summing the electronic signals 16 from one of the plurality of cardiac cycles of the livo phase. The user then generates on the video monitor 50 an end diastole and an end systole mask characteristic of the boundary line of each image data frame after noise and background correction. The operator further creates a composite mask by combining the end diastole and end systole masks. The operator uses the computer system 34 in conjunction with the computer software and applies the composite mask to all the image data frames in the livo phase by setting to zero all data values of the electronic signal 16 outside the composite mask. The resulting masked image data frames of the electronic signals 16 are deinterpolated to the original array of $20 \times 20$ pixel values, and the centroid is calculated for each $20 \times 20$ image data frame. The composite mask is then applied to the representative, or composite, image data frames made up of the characteristic time segments of the summed plurality of cardiac cycles. This step is followed by deintepolation to the $20 \times 20$ array of pixel values for the plurality of representative image data frames. The centroid of each of the image data frames of the processed electronic signals 16 are repositioned to the centroid of the corresponding associated (same phase of the cardiac cycle) representative image data frame. This repositioning achieves the desired motion correction to obtain the video signals (the motion corrected form of the electronic signals 16). Therefore, for example, the centroid of the plurality of the electronic signals 16 making up the end diastole image data frames is repositioned to the centroid of the end diastole of the representative image data frame. This functionality is readily achieved for each associated phase of the plurality of cardiac cycles.

Figure 3A:
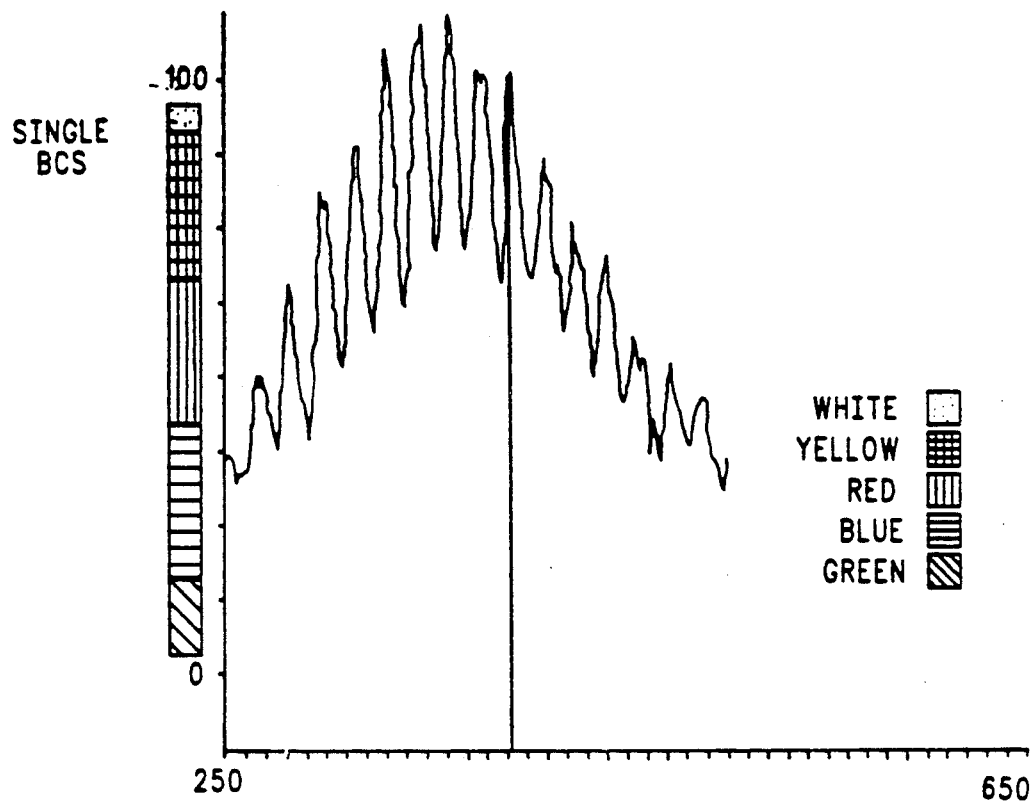
FIG. 3A shows a histogram after motion correction of electronic signal amplitudes for a plurality of cardiac cycles in a designated livo phase.

FIGS. 2A and 3A illustrate before and after completion of the motion correction methodology. The major indication of an improvement in the data quality is the smoothing of the trace of the minimums of the plurality of cardiac cycles. The maximums are not nearly so sensitive a figure of merit of the degree of motion correction. The data associated with these figures is set forth in detail on an attachment to the microfiche appendix.

In other forms of the above described invention, the method of correcting for patient body motion can be extended to remove artifacts introduced when performing other than first pass radionuclide angiography, such as, for example, gated equilibrium radionuclide angiography or myocardial perfusion imaging (see, for example, the method and system of U.S. Pat. No. 4,585,008 which is incorporated by reference herein). Such methodologies can be used to generate a dynamic set of image data frames of fluid flow (liquid or gas, for example) within the body of a patient who is moving, voluntarily or even involuntarily in some cases, such as patient coughing or the like. Data which is characteristic of fluid flow can arise not only from a radioactive fluid within the patient's body, but also from other conventional radiographic methods, such as injecting a contrast medium which absorbs X-rays (a Barium containing material, for example), or gamma rays or particles (neutrons, protons, positrons, for example) passing through the patient. Sources of X-rays, gamma rays or particles are readily available and can be added to the system shown in FIG. 1. One example of such a system is set forth in U.S. Pat. No. 4,483,342 which is incorporated by reference herein. These radiations are conventionally sensed by an appropriate detector, such as a solid state electronic detector or a nuclear particle detector. Once the electronic signal 16 has been generated by the detector, the advantageous methods of the subject invention for data analysis and motion removal can be applied as explained hereinbefore.

While there has been illustrated herein various embodiments illustrative of the present invention, modifications of the present form of the invention will be apparent after study. As such the scope of the invention should not be limited by the particular embodiments and construction disclosed herein, but should be defined by the appended claims and equivalents thereof.

What is claimed is:

1. A method of generating a dynamic set of angiographic images of image flow within the body of a patient undergoing motion, comprising the steps of:

injecting a radioactive dye into the patient;

detecting from a selected spatial area of the patient's body radiation emitted by said radioactive dye circulating within the patient while the patient is in motion;

generating an electronic signal from said detected radiation, said electronic signal including a plurality of time segmented image data frames representing the time segment portions of complete cardiac cycles associated with the amount of said radioactive dye circulating through said selected spatial area of the patient's body;

manipulating said electronic signal to generate a video signal characteristic of said angiographic images being substantially free of the effect of the patient motion, said step of manipulating said electronic signal comprising, (a) selecting a livo phase comprising a plurality of said electronic signals in a plurality of said image data frames associated with the time varying passage through the patient of said radioactive dye during a plurality of sequential cardiac cycles;

(b) generating an integrated electronic signal by summing said electronic signals from said plurality of cardiac cycles in said selected livo phase;

(c) selecting a threshold data level for said intergrated electronic signal;

(d) applying said threshold data level to said integrated electronic signal for creating a mask boundary for a selected systole image and for a selected diastole image;

(e) generating a composite mask boundary by combining said selected systole mask boundary and said diastole mask boundary;

(f) applying said composite mask boundary to said integrated electronic signal and to each of said plurality of said livo phase image data frames of said electronic signals and setting to zero said integrated electronic signal and said electronic signals outside of said composite mask boundary in each of said image data frames within each of said plurality of cardiac cycles;

(g) calculating the area centroid of said integrated electronic signal in said image data frames and said livo phase electronic signals in each of said associated image data frames of said plurality of cardiac cycles;

(h) dividing said livo phase electronic signals and said integrated electronic signal into said angiographic image data frames representing the parts of the complete cardiac cycle; and (i) generating said video signals by repositioning the spatial location of said livo phase electronic signals within said image data frames by moving the centroid of said electronic signals of each of said data frames to the centroid of said image data frames of said integrated electronic signals, said repositioning performed for each corresponding associated said image data frame within each of said phases of the cardiac cycle.

2. A method of generating a dynamic set of images of fluid flow within an exercising patient, comprising the steps of:

injecting a radioactive fluid into the patient's body;

detecting from a selected area of the patient's body radiation emitted from said radioactive fluid while the patient is exercising;

generating a plurality of time segmented image data frames of electronic signals arising from the detection of said radiation emitted from said radioactive fluid;

selecting a region of interest for said image data frames, generating a histogram of image data frames for a plurality of cardiac cycles and selecting the starting and ending ones of said cardiac cycles for marking the boundaries of said livo phase;

selecting a representative one of cardiac cycles in said livo phase and generating a composite cardiac image data frame by summing all of electronic signals in said representative cardiac cycle;

determining the centroid of said composite image data frame and the centroid in each of said image date frames of said electronic signals over said plurality of cardiac cycles in said livo phase; and repositioning the spatial location of electronic signals within each of said image data frames of said plurality of cardiac cycles by moving the centroid of said electronic signals in said image data frames to the centroid of said composite image data frame.

3. The method as defined in claim 2 further including the step of selecting a threshold background signal and removing said threshold background signal from said composite image data frame and from said image data frames of said electronic signals over said plurality of cardiac cycles in said livo phase.

4. A method of generating a dynamic set of angiographic images of fluid flow through a patient whose body is in motion, comprising the steps of:

injecting a radioactive contrast medium into the patient's body;

generating a radiation beam for passing through the patient's body for indicating the amount of said radiation contrast medium flowing through selected portions of the patient's body;

detecting a portion of said radiation beam passed through the patient's body;

generating an electronic signal from detection of said radiation beam;

processing said electronic signal to generate over a cardiac cycle a plurality of time segmented image data frames representing the time segment portions of complete cardiac cycles associated with the amount of said radiation contrast medium flowing through said selected portions of the patient's body;

processing said electronic signal to generate a video signal characteristic of said angiographic images being substantially free of the effect of the patient motion, said step of processing said electronic signal comprising, (a) selecting a livo phase comprising a plurality of said electronic signals in a plurality of said image data frames associated with the time varying passage through the patient's cardiac system of said contrast medium during a plurality of sequential cardiac cycles;

(b) generating an integrated electronic signal by summing said electronic signals from said plurality of cardiac cycles in said selected livo phase;

(c) selecting a threshold data level for said intergrated electronic signal;

(d) applying said threshold data level to said integrated electronic signal for creating a mask boundary for a selected systole image and for a selected diastole image;

(e) generating a composite mask boundary by combining said selected systole mask boundary and said diastole mask boundary;

(f) applying said composite mask boundary to said integrated electronic signal and to each of said plurality of said livo phase image data frames of said electronic signals and setting to zero said integrated electronic signal and said electronic signals outside of said composite mask boundary in each of said image data frames within each of said plurality of cardiac cycles;

(g) calculating the area centroid of said integrated electronic signal in said image data frames and said livo phase electronic signals in each of said associated image data frames of said plurality of cardiac cycles;

(h) dividing said livo phase electronic signals and said integrated electronic signal into said image data frames representing the part of the complete cardiac cycle; and (i) generating said video signals by repositioning the spatial location of said livo phase electronic signals within said image data frames by moving the centroid of said electronic signals of each of said data frames to the centroid of said image data frames of said integrated electronic signals, said repositioning performed for each corresponding associated said image data frame within each of said phases of the cardiac cycle.

5. The method as defined in claim 4 wherein said exercise comprises bicycling.

6. The method as defined in claim 4 wherein said radiation contrast medium comprises an X-ray absorbing material.

7. The method as defined in claim 4 wherein said radiation beam is at least one of a neutron beam, an X-ray beam and a position beam and said radiation contrast medium comprises a material absorbent of said radiation beam.

8. A method of generating a dynamic set of angiographic images of fluid flow within the body of a patient undergoing motion, comprising the steps of:

injecting a radioactive dye into the patient;

detecting from a selected spatial area of the patient's body radiation emitted by said radioactive dye circulating within the patient while the patient is in motion;

generating an electronic signal from said detected radiation, said electronic signal including a plurality of time segmented image data frames representing the time segment portions of complete cardiac cycles associated with the amount of said radioactive dye circulating through said selected spatial area of the patient's body;

manipulating said electronic signal to generate a video signal characteristic of said angiographic images being substantially free of the effect of the patient motion, said step of manipulating said electronic signal comprising, (a) selecting a livo phase comprising a plurality of said electronic signals in a plurality of said image data frames associated with the time varying passage through the patient of said radioactive dye during a plurality of sequential cardiac cycles;

(b) generating an integrated electronic signal by summing said electronic signals from said plurality of cardiac cycles in said selected livo phase;

(c) generating a mask boundary denoting a region of interest in said angiographic images;

(d) applying said mask boundary to said integrated electronic signal and to each of said plurality of said livo phase image data frames of said electronic signals and setting to zero said integrated electronic signal and said electronic signals outside of said mask boundary in each of said image data frames within each of said plurality of cardiac cycles;

(e) calculating the area centroid of said integrated electronic signal in said image data frames and the area centroid of said livo phase electronic signals in each of said associated image data frames of said plurality of cardiac cycles;

(f) dividing said livo phase electronic signals and said integrated electronic signal into said image data frames representing the parts of the complete cardiac cycle; and (g) generating said video signals by repositioning the spatial location of said livo phase electronic signals within said image data frames by moving the centroid of said electronic signals of each of said data frames to the centroid of said image data frames of said integrated electronic signals, said repositioning performed for each corresponding associated said image data frame within each of said phases of the cardiac cycle.

9. The method as defined in claim 8 wherein said region of interest is the ventricle region of the patient's cardiac system.

10. A method of generating a dynamic set of images of fluid flow within an exercising patient, comprising the steps of:

injecting a contrast medium into the patient's body;

generating a radiation beam passing through the patient's body to detect the passage of said radiation contrast medium flowing through selected portions of the patient's body;

detecting a portion of said radiation beam passed through the patient's body;

generating an electronic signal from detection of said radiation beam;

generating a plurality of time segmented image data frames of electronic signals arising from the detection of said radiation beam passed through the patient's body establishing the boundaries of said livo phase by selecting a region of interest in said image data frames, generating a histogram of image data frames for a plurality of cardiac cycles and selecting the starting and ending ones of said cardiac cycles;

selecting a representative one of the cardiac cycles in said livo phase and generating a composite cardiac image data frame by summing all of said electronic signals in said representative cardiac cycle;

determining the centroid of said composite image data frame and the centroid in each of said image data frames of said electronic signals over said plurality of cardiac cycles in said livo phase; and repositioning the spatial location of the electronic signals within each of said image data frames of said plurality of cardiac cycles by moving the centroid of the electronic signals in said image data frames to the centroid of said composite image data frame.

11. The method as defined in claim 10 further including the step of selecting a threshold background signal and removing said threshold background signal from said composite image data frame and from said image data frames of said electronic signals over said plurality of cardiac cycles in said livo phase.

* * * * *